United States Patent
Dinsmoor et al.

(10) Patent No.: US 11,559,258 B2
(45) Date of Patent: Jan. 24, 2023

(54) STIMULATION LEAD WITH ELECTRODES CONFIGURED FOR SENSING AND STIMULATION OVER A PARTIAL CIRCUMFERENCE

(71) Applicant: Medtronic, Inc., Minneapolis, MN (US)

(72) Inventors: David A. Dinsmoor, St. Paul, MN (US); Jiashu Li, Mounds View, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 328 days.

(21) Appl. No.: 16/862,732

(22) Filed: Apr. 30, 2020

(65) Prior Publication Data
US 2021/0339014 A1   Nov. 4, 2021

(51) Int. Cl.
*A61N 1/36* (2006.01)
*A61B 5/00* (2006.01)
*A61B 5/24* (2021.01)

(52) U.S. Cl.
CPC .............. *A61B 5/6877* (2013.01); *A61B 5/24* (2021.01); *A61B 5/686* (2013.01); *A61N 1/36071* (2013.01); *A61N 1/36139* (2013.01)

(58) Field of Classification Search
None
See application file for complete search history.

(56) References Cited

U.S. PATENT DOCUMENTS

| 6,510,347 B2 | 1/2003 | Borkan |
| 9,656,085 B2 | 5/2017 | Moffitt et al. |
| 9,814,880 B2 | 11/2017 | Hershey et al. |
| 2009/0054946 A1* | 2/2009 | Sommer ............ A61N 1/36185 607/59 |
| 2015/0066120 A1* | 3/2015 | Govea .................. A61N 1/0534 607/116 |
| 2015/0073518 A1* | 3/2015 | Conroy .................... A61N 1/05 607/116 |
| 2015/0360031 A1* | 12/2015 | Bornzin ............. A61N 1/36139 607/62 |
| 2016/0206883 A1 | 7/2016 | Bornzin et al. |
| 2018/0078769 A1 | 3/2018 | Dinsmoor et al. |
| 2018/0228547 A1 | 8/2018 | Parker et al. |

(Continued)

OTHER PUBLICATIONS

International Search Report and Written Opinion from PCT Application No. PCT/US2021/026941 dated Aug. 25, 2021, 15 pages.

(Continued)

*Primary Examiner* — Paula J Stice
(74) *Attorney, Agent, or Firm* — Mueting Raasch Group

(57) ABSTRACT

A lead body is operable to be implanted proximate a target nerve tissue of a patient. A sensing electrode is configured to sense biopotentials over a first partial circumference of the lead body. A stimulation electrode is configured to deliver stimulation energy over a second partial circumference of the lead body. A signal generator is electrically coupled to the stimulation electrode and a sensing circuit is coupled to the sensing electrode. A processor is operable to apply a stimulation signal to the stimulation electrode via the signal generator and, via the sensing circuit, sense an evoked response to the stimulation signal that propagates along a neural pathway.

22 Claims, 9 Drawing Sheets

(56) References Cited

U.S. PATENT DOCUMENTS

| | | |
|---|---|---|
| 2019/0030339 A1 | 1/2019 | Baru et al. |
| 2019/0060634 A1* | 2/2019 | Skubitz .................... A61N 1/05 |
| 2019/0099602 A1 | 4/2019 | Esteller et al. |
| 2019/0142325 A1 | 5/2019 | Min et al. |
| 2019/0275334 A1 | 9/2019 | Hou et al. |
| 2019/0366094 A1 | 12/2019 | Esteller et al. |
| 2019/0388695 A1 | 12/2019 | Dinsmoor et al. |
| 2020/0009374 A1 | 1/2020 | Howard et al. |
| 2020/0179675 A1* | 6/2020 | Cass .................... A61N 1/0488 |

OTHER PUBLICATIONS

International Search Report and Written Opinion from PCT Application No. PCT/US2021/026940 dated Jul. 12, 2021, 14 pages.

* cited by examiner

Section A-A

STIMULATION LEAD WITH ELECTRODES CONFIGURED FOR SENSING AND STIMULATION OVER A PARTIAL CIRCUMFERENCE

SUMMARY

The present disclosure relates to a stimulation lead with electrodes configured for sensing and stimulation over a partial circumference. In one embodiment, a system includes a lead body operable to be implanted proximate a target nerve tissue of a patient. The system includes a sensing electrode and a stimulation electrode disposed on the lead body and separated longitudinally along the lead body. Both the sensing and stimulation electrodes include ring electrodes partially covered with an insulator such that the ring electrodes sense and emit electrical fields along partial circumferences of the lead body not covered by the insulator. The system includes a signal generator electrically coupled to the stimulation electrode and a sensing circuit coupled to the sensing electrode. A processor of the system is coupled to the signal generator and the sensing circuit and operable to: apply a stimulation signal to the stimulation electrode via the signal generator; and via the sensing circuit, sense from the sensing electrode an evoked response to the stimulation signal that propagates along a neural pathway.

In another embodiment, a method involves repeatedly performing a test operation via a processor over a plurality of rotation angles of a lead. The lead includes a sensing electrode and a stimulation electrode disposed on a lead body and separated longitudinally along the lead. Both the sensing and stimulation electrodes respectively sense and emit electrical fields along partial circumferences of the lead. The test operation involves for each of the rotation angles: applying a stimulation signal to the stimulation electrode and sensing from the sensing electrode an evoked response to the stimulation signal that propagates along a neural pathway; recording a characteristic of the evoked response that indicates an effectiveness of at least one of application of the stimulation signal and the sensing of the evoked response at the rotation angle. The method involves, via the processor, determining from the characteristics recorded during the test operations a selected rotation angle of the lead that results in effective performance of the lead. The selected rotation angle facilitates affixing the lead in the epidural space.

These and other features and aspects of various embodiments may be understood in view of the following detailed discussion and accompanying drawings.

BRIEF DESCRIPTION OF THE DRAWINGS

The discussion below makes reference to the following figures, wherein the same reference number may be used to identify the similar/same component in multiple figures.

DETAILED DESCRIPTION

Figure 1:
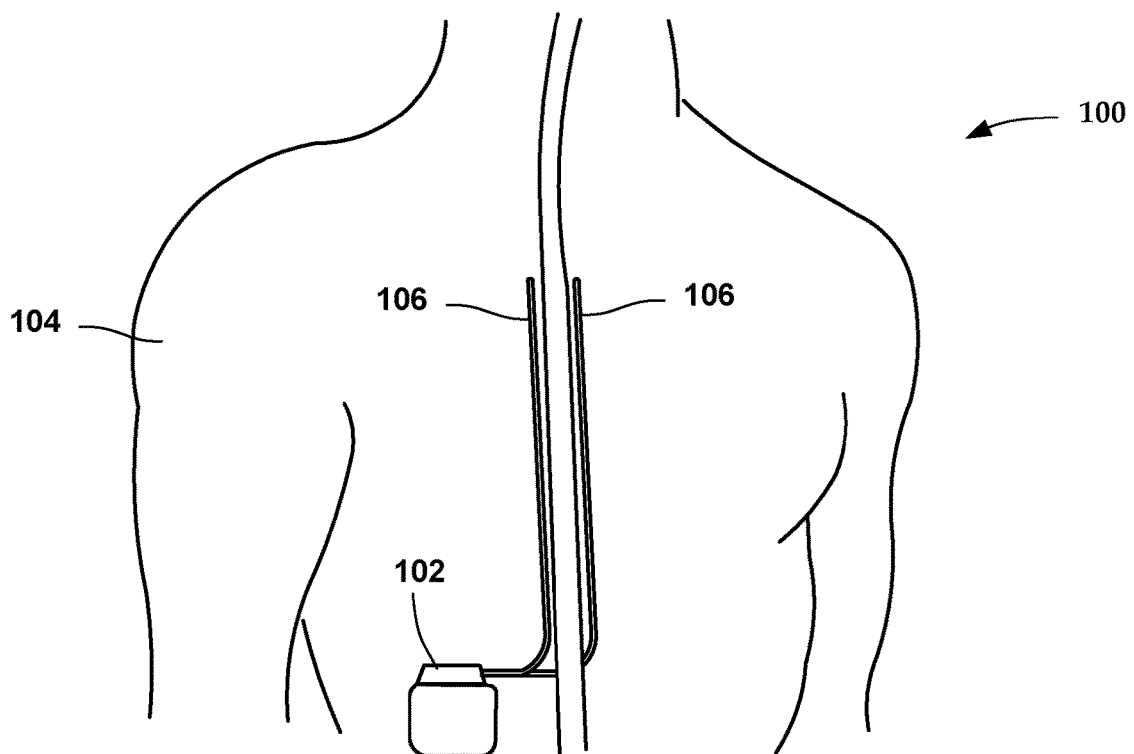
FIG. 1 is a simplified diagram of an implantable system according to an example embodiment.

The present disclosure is generally related to electrical stimulation therapy. Medical devices may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, gastroparesis, etc. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

These therapies can be delivered using a percutaneous stimulation lead. In some implementations, a percutaneous stimulation lead has cylindrical electrodes arrayed longitudinally along a lead body. Electrical stimulation therapy may be delivered by applying a series of electrical stimulation pulses to a selected set of the electrodes. In some types of therapy, some of the electrodes on the lead can be configured to sense an evoked compound action potential (ECAP) to the stimulation pulses. The stimulation pulses may be therapeutic or non-therapeutic, and the sensed ECAP response facilitates measuring the efficacy of the applied pulses. The ECAP measurements can be used to adjust the therapy (e.g., pulse width, amplitude, frequency, overshoot) to improve the efficacy of the treatment. The measurement of the ECAP response allows for, among other things, the manual or automatic adjustment of the implantable device to compensate for changing conditions over the life of the device. Examples of changing conditions include shifting of position/orientation of the lead within the body, changing physiology of the patients, etc.

In some implementations, the percutaneous stimulation lead body is an elongated cylindrical tube, which can be implanted using relatively non-intrusive surgical procedures. The electrodes on such a lead may be cylindrical rings array longitudinally down the length of the lead. To provide the therapy, two or more electrodes may be configured to provide stimulation therapy, e.g., being electrically coupled to respective positive and negative outputs of a pulse generator. For an ECAP process, two or more different electrodes (e.g., at a distal end of the lead) segments may be electrically coupled to sense the evoked response, with one electrode being coupled as an anode and the other as a cathode. The lead may have any number of electrodes (e.g., more than four) electrodes to allow for customizing the location of the stimulation and sensing. This customization can be performed electronically by the selection of different subsets of the electrodes for each function, e.g., using a switching circuit.

Percutaneous, epidural, cylindrical electrodes for spinal cord stimulation may provide poor targeting of the stimulation field to the target neural structures. For therapies such as spinal cord stimulation, the lead may be positioned in an epidural space near the dorsal column of the patient's spine. In this location, one side of the lead is facing the nerve tissue of the spinal cord. The part of the stimulation electrodes facing away from the spinal cord are emitting into tissue that is not being treated, and the part of the sensing electrodes facing away from the spinal cord are picking up electromagnetic impulses that may not be related to the treatment.

In some embodiments described herein, subcutaneous lead electrodes are configured to sense and emit electromagnetic fields over a first partial circumference of the lead body, such that there is no respective sensing and emission along second partial circumference at the same longitudinal location. The second partial circumference is different than the first partial circumference, e.g., the partial circumferences may be non-overlapping. This may be achieved by segmenting the electrodes at each longitudinal location, and/or by covering parts of fully circumferential electrodes (e.g., ring electrodes) with an electrical insulator that suppresses emission/sensing along the covered portions.

In FIG. 1, a diagram illustrates a system 100 according to an example embodiment. The system includes an implantable therapy device 102 configured to deliver electrical stimulation therapy to patient 104. In the illustrated example, the therapy device 102 is configured to deliver spinal cord stimulation therapy using devices and methods described herein. Although the methods and apparatuses described in this disclosure are generally applicable to a variety of medical devices including external and implantable medical devices, embodiments of implantable electrical stimulators (e.g., neurostimulators) will be described for purposes of illustration. For example, an implantable spinal cord stimulation system 100 is shown for purposes of illustration, but without limitation as to other types of medical devices or other therapeutic applications of medical devices.

As shown in FIG. 1, the implantable device 102 is electrically coupled to one or more leads 106. The implantable device 102 is configured as an electrical stimulator that generates and delivers electrical stimulation therapy to patient 104 via electrodes of leads 106, e.g., for relief of chronic pain or other symptoms. The implantable device 102 may use more or fewer leads 106.

In addition to electrical stimulation therapy, the implantable device 102 may also be configured to generate and deliver control pulses configured to elicit ECAP signals that may or may not contribute to the therapy of informed pulses. As discussed herein, the control pulses may be non-therapeutic. The implantable device 102 may be a chronic electrical stimulator that remains implanted within patient 105 on the order of weeks to years. The implantable device 102 may be a temporary, or trial, stimulator used to screen or evaluate the efficacy of electrical stimulation for chronic therapy. In one example, implantable device 102 is implanted within patient 104, while in another example, implantable device 102 is an external device coupled to percutaneously implanted leads 106.

Figure 2:
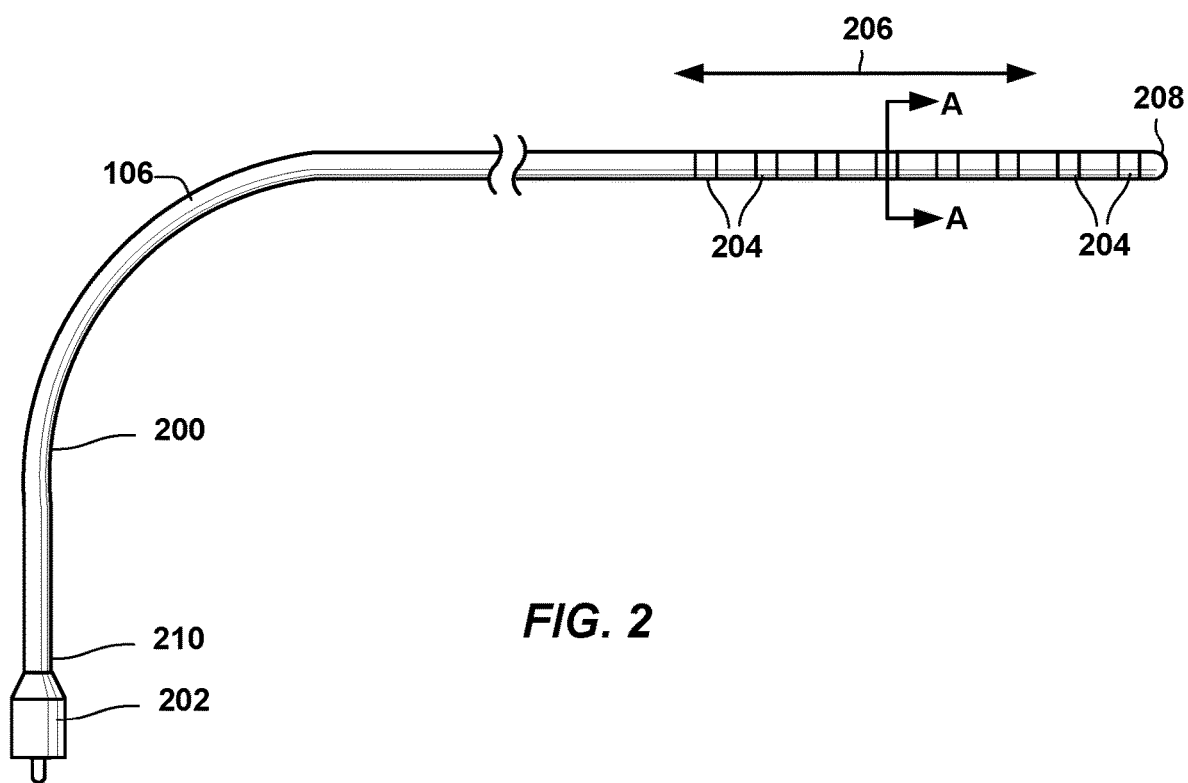
FIG. 2 is a side view of an implantable lead according to an example embodiment.

In FIG. 2, a side view illustrates features of a percutaneous lead 106 for stimulation therapy according to various embodiments. The lead 106 includes a lead body 200 that is generally a flexible tube configured to carry electrical conductors within (not shown). A connector 202 is at a proximal end 210 of the lead body 200 and provides electrical coupling to the implantable device 102 shown in FIG. 1. Generally, a centerline of the lead body 200 defines a longitudinal direction of the lead 106, as indicated by line 206 near a distal end 208 of the lead body 200. Electrodes 204 are disposed on an outer surface of the lead body 204 and offset from one another in the longitudinal direction 206.

Figure 3:
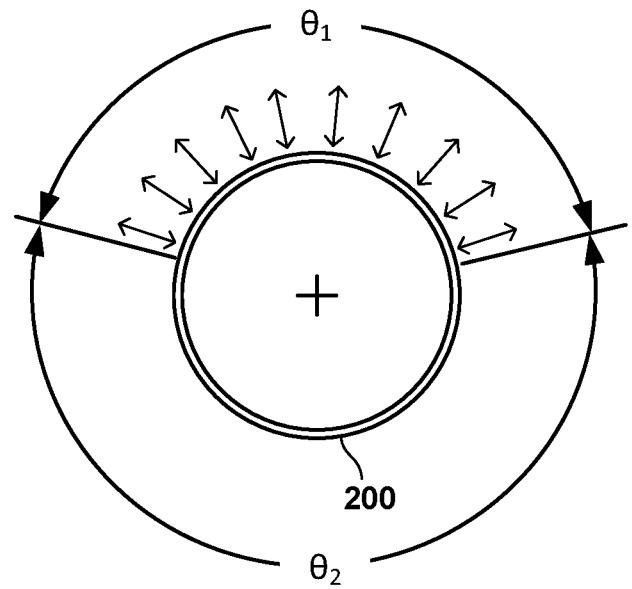
FIG. 3 is a cross-sectional view of the lead shown in FIG. 2.

As noted above, the electrodes 204 are capable, e.g., when configured to provide stimulation therapy, emit over a partial circumference around the lead body 200. Similarly, when the electrodes 204 are configured as sensors, they are capable of sensing over a partial circumference of the lead body 200. In FIG. 3, a cross sectional view of the lead body 300 shows, in one embodiment, how electrodes (not shown) are configured to emit or sense over a first partial circumferential angle $\theta_1$ while there is no (or limited) emission or sensing over a second partial angle $\theta_2$. There may be multiple, discontinuous angles $\theta_1$, $\theta_2$, and in some embodiments the angles $\theta_1$, $\theta_2$ may be changed via operational inputs that affect signal lines electrically coupled to the lead 200. In some embodiments, $\theta_1$ may be between 10 degrees and 300 degrees, and $\theta_2$ may be between 60 degrees and 350 degrees.

Figure 4:
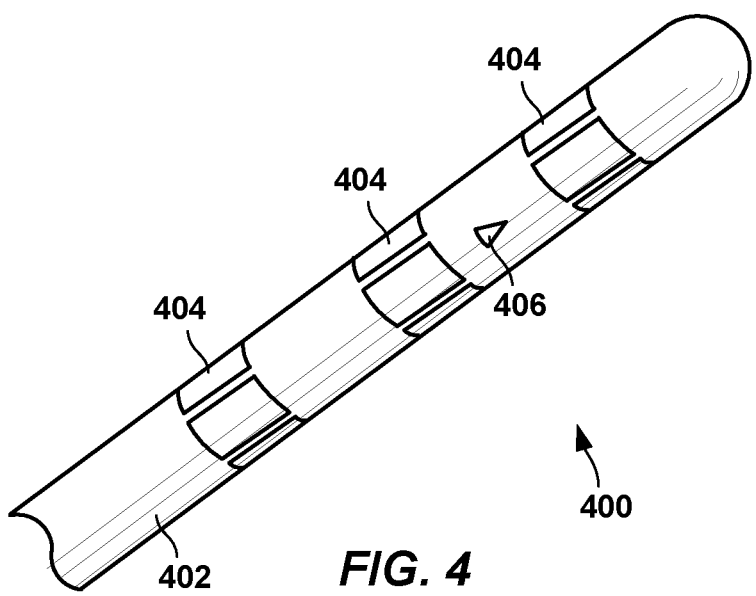
FIG. 4 is an isometric view of a lead according to an example embodiment.

In some examples, segmented leads may provide partial stimulation/sensing shown in FIG. 3. In FIG. 4, a perspective view shows a segmented lead 400 according to an example embodiment. The lead 400 includes a lead body 402, on which are located segmented electrodes 404. The cylindrical electrodes 404 are broken into cylindrical segments to which current may be delivered in a fractionalized manner. The size and number of segments of electrodes 404 may be configured as described below in FIG. 5, as well as the size and configuration of gaps between the segments, One or more radiopaque azimuth markers 406 may be incorporated into the lead 400 so as to provide the lead implanter a means to determine alignment. The markers 406 may be located on an outer surface of the lead proximate where the electrodes 404 are longitudinally located on the lead body. Multiple markers 406 may be used at different longitudinal locations and at the same longitudinal location. For example, two markers 406 may be located 180 degrees from each other at one or more longitudinal locations, three markers 406 may be located 120 degrees from each other at one or more longitudinal locations, etc. In other embodiments, the markers 406 may be non-symmetrically arrayed at one longitudinal location.

Current may be delivered independently to the cylindrical segments on each electrode 404, and segments not used for stimulation may be employed for biopotential sensing. The electronics connected to these segments may include switchable elements which balance the path impedance between the electrodes and the sensing circuitry. These elements may be employed to maximize a common mode rejection ratio, for instance. Further, use of a subset of the segments, e.g., to deliver stimulation therapy, may require less power from a therapy signal generator than an omnidirectional lead while providing similar results.

A segmented electrode lead 400 may be operably coupled to a controller for placing, trialing, and optimizing the lead location and electrode choices in the patient. These features may be employed to enhance sensing capabilities of biopotentials in the spine, such as the evoked compound action potential (ECAP). Because the emission of electromagnetic fields can be limited to partial periphery of the lead 400, the lead can precisely deliver stimulation energy to the neural target, e.g., the dorsal column of the spine, versus an omnidirectional space that includes epidural fat and ligament. This can lead to better therapeutic outcomes (e.g., enhanced activation in the midline dorsal columns) and reduced side effects (e.g., nerve root stimulation). Conversely, stimulation may intentionally be delivered to a target which has no physiologic effect. This may be of utility when doing a placebo controlled clinical trial, for instance.

By using a lead with segmented electrodes as shown in FIG. 4, an evoked response-equivalent can be generated at a subset of the segments using less stimulation current than would be needed if the stimulation current was applied to all segments or to an equivalently sized and located ring electrode. The response can be detected using an omnidirectional electrode (not shown) or a segmented electrode on the same lead 400. This can decrease the burden for patients with rechargeable neurostimulators due to lower power use, for example. This can also reduce the power used for non-ECAP functions. Such an arrangement can also reduce stimulation artifacts which interfere with biopotential sensing.

Figure 5:
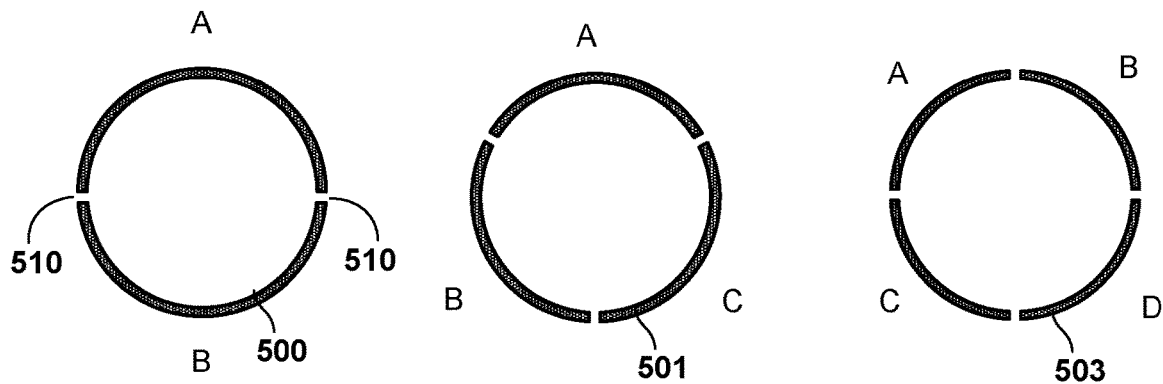
FIG. 5 is a set of cross-sectional views of segmented electrodes according to different example embodiments.

In FIG. 5, a cross sectional view illustrates segmented electrodes that can be used on a lead according to example embodiments. Electrode 500 has two segments A, B, each covering approximately 180°. In practice, the sum of coverage angles for the segments in this and other embodiments will be somewhat less than 360° due to the inclusion of gaps 510 between adjacent segments. Electrode 501 has three segments A-C each covering approximately 120° and electrode 502 has three segments A-C each covering approximately 90°. Note that in some embodiments, a subset of these electrode segments may be manufactured at a particular location. For example, at one or more locations, a lead could stimulate using an electrode with segments A and B of electrode 503 but without stimulating using segments C or D. Any number of permutations according to the number of segments are possible.

Note that while the term "electrode" in some examples is used to refer to a collection of segments at a common longitudinal location on a lead body, each of the segments may be themselves operable as individual electrodes, e.g., being independently electrically coupled and decoupled from stimulation and sensing circuitry, and with different values of voltage and/or current applied during activation. In some embodiments, two or more of the segments may be commonly coupled to be in the same activation state, such that they collectively behave as a single electrode. Even in this state, individual segments may have different electrical path properties (e.g., impedance, applied stimulation voltage/current, bias currents, etc.) applied by the switching element to which the segments are coupled.

While the electrodes 500-502 are all shown with equal size segments (e.g., segments A-D in electrode 503 are all close to 90°), in other embodiments the segments could be of differing size, and the gaps that separate the segments may have different dimensions. For example, for electrode 500, segment A could cover a 265° angle, segment B could cover a 90° angle, and the left and right gaps 510 could cover 1° and 4° angles, respectively.

A neurostimulation lead may include anywhere from 2 to 16 of these segmented electrodes, although any number may be used. For instance, a lead with eight 4-segment electrodes (E0-E7, where E0 is closest to the distal end of the lead and E7 is closest to the proximal end) would have 32 individually addressable segments. Note that a lead may use different numbers of segments and different locations. For example, E0 and E1 (often used for sensing near the distal end) may use a 2-segment electrode 500 while the other locations (often used for stimulation) may use a 4-segment electrode 503. Other combinations are possible, including combinations with a non-segmented, fully cylindrical electrode at some locations and/or in combination with masked directional leads that are described in greater detail below. For example, a segmented electrode such as electrode 501 could be longitudinally proximate to but separated from a second electrode that is an unsegmented ring electrode. One segment of the segmented electrode 501 could be coupled an anode/cathode for purposes of stimulation or sensing, and the unsegmented electrode could be coupled as the cathode/anode circuit return path.

Figure 6:
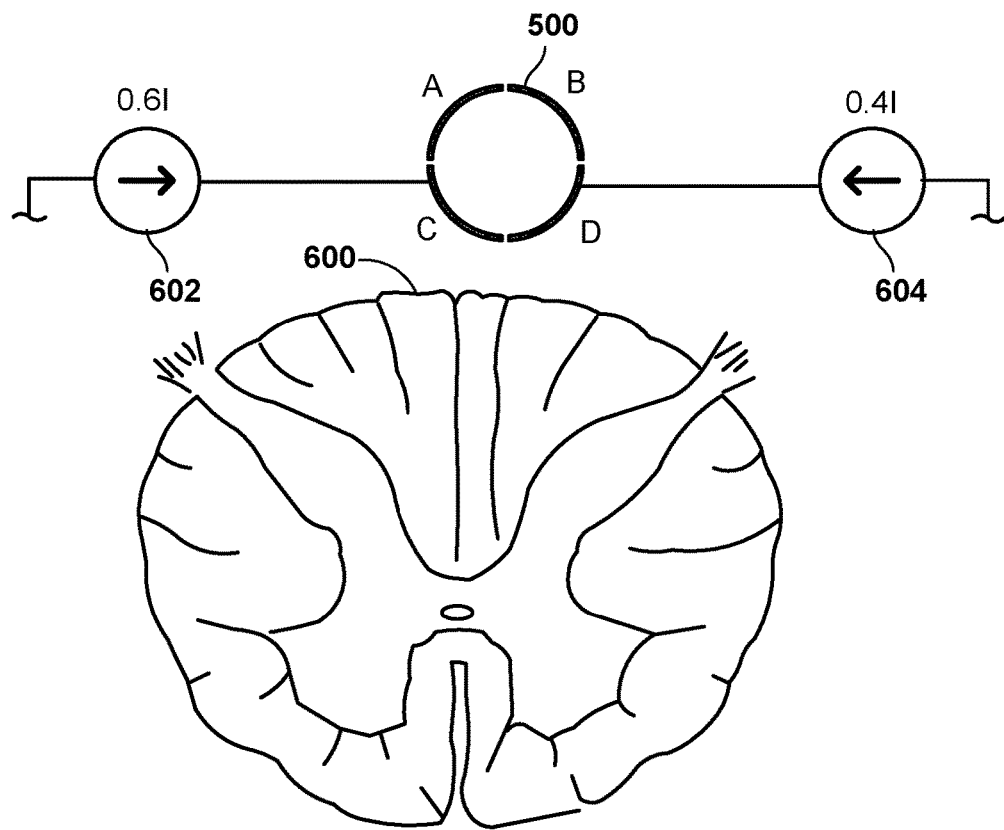
FIG. 6 is a schematic diagram illustrating application of fractional currents to a segmented electrode according to an example embodiment.

Stimulation may be delivered through segments of the electrodes to maximize or minimize a particular neurophysiologic effect, or associated phenomena such as stimulation artifact. An example of this is shown in FIG. 6, which is a diagram of segmented electrode 500 being used according to an example embodiment. The electrode 500 (e.g., E6 of a lead with eight 4-segment electrodes) is positioned to the right of midline from the dorsal columns 600 at T8 as shown in FIG. 6. Balanced paresthesia across the mid-back is obtained in the subject by fractionalizing the cathodic pulse with 60% of the current (as indicated by current source 602) through segment C and 40% through segment D (as indicated by current source 604). Sensing is selected to occur on E1+/E0− (not shown), wherein all cylindrical segments of each respective segmented electrode are ganged together (assuming E0 and E1 are also segmented).

Figure 7:
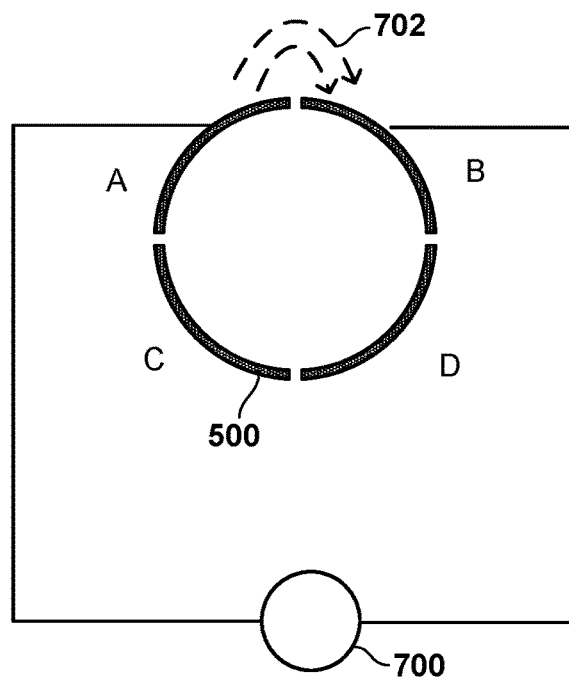
FIG. 7 is a schematic diagram illustrating creation of a field between adjacent segments of an electrode according to an example embodiment.

The stimulation anode (not shown) may be configured as a similar segmental configuration on E7 (e.g., so as to deliver bipolar stimulation), or it may use other segments on the same segmented electrode 500, in this case segments A and B on electrode 500 could be used as a stimulation anode. Using segments on the same segmented electrode as both the cathode and anode is particularly advantageous when sensing evoked potentials, as it sets up the stimulation gradient (and subsequently the artifact), which confounds evoked potential sensing perpendicular to a sensing vector on E1/E0. This enhances the ability of the sensing electronics to resolve the evoked potential from stimulation artifacts versus stimulation/sensing configurations wherein the stimulating electrodes are arrayed linearly with respect to the sensing electrodes. In FIG. 7, a diagram shows another example of using segments of the same segmented electrode for anode and cathode. In this example, a circuit element 700 is coupled between segments A and B. If the circuit element 700 is a current source, this will result in emitting the field 702 between segments A and B. If the circuit element 700 is a sensor, the sensor will detect a field 702 between segments A and B.

As noted above, the stimulation of nerve tissue to evoke an ECAP response can result in stimulation artifacts being detected at the sensing electrodes. These artifacts are generally due to the applied pulse traveling through tissue that is surrounding the lead away from the target nerve tissue. Because this surrounding nerve tissue is somewhat electrically conductive, the applied pulse can be seen at the sensing electrode. This artifact can sometimes superimposed over or otherwise interfere with the evoked responses that are also being sensed at or near the same time. As noted above, using portions of a stimulation electrode that emit over a partial circumference directed at the target nerve tissue can reduce the amplitude of these artifacts. Similarly, using portions of sensing electrodes that are facing the target nerve tissue can help further reduce the amplitude of the artifacts. However, there may still be some stimulation artifacts seen at the sensing electrode, and in some embodiments, the lead can be configured to isolate and characterize the artifacts to assist in signal processing of the response signals.

Figure 8:
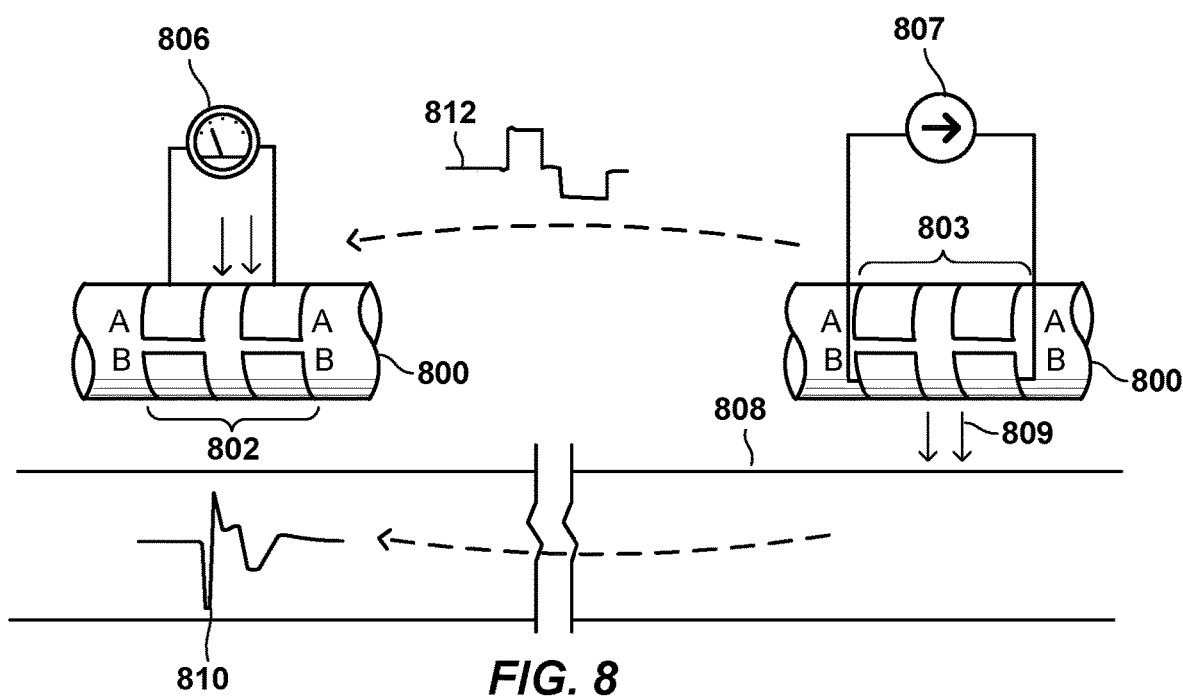
FIG. 8 is a schematic diagram showing the use of segmented electrodes to measure stimulation artifacts according to an example embodiment.

In FIG. 8, a diagram shows an example of a configuration that can be used to identify/characterize stimulation artifacts according to an example embodiment. Two portions of a lead 800 are shown, each portion having respective pairs of segmented electrodes 802, 803. Segments A of electrode pair 802 are set up as sensing electrode, as indicated schematically by voltmeter 806. Segments B of electrode pair 803 are set up as stimulation electrodes, as indicated schematically by current source 807. The segments B of stimulation electrode 803 are facing target nerve tissue 808, while segments A of sensing electrode 802 are facing away from the target nerve tissue 808.

The application of an electrical field 809 via stimulation electrode 803 results in an ECAP response 810 through the target tissue 808. At the same time, the electrical field induces a stimulation artifact 812 through the surrounding tissue. The stimulation artifact 812 resembles the pulse waveform used to induce the ECAP response 810, although will be changed due to characteristics of the signal transmission path through the surrounding tissue. In this example, the segments A of the sensing electrode pair 802 face away from the target nerve tissue 808, and therefore will sense the artifact 812 signal with greater sensing amplitude than it will sense the ECAP response signal 810. Facing the segments away from the target nerve tissue 808 facilitates decoupling the artifact 812 from ECAP responses generated along the target nerve tissue 808. Accordingly, the therapy system utilizing the lead 808 can characterize the artifact signal 812 near the sensing electrodes 802, e.g., in terms of phase/delay, amplitude, etc. These characteristics can be recorded and used in subsequent signal processing of the ECAP response 810, e.g., via segments B of electrode pair 802. Note that this embodiment may be used with a single segmented electrode as seen in FIG. 7 instead of electrode pairs.

Figure 9:
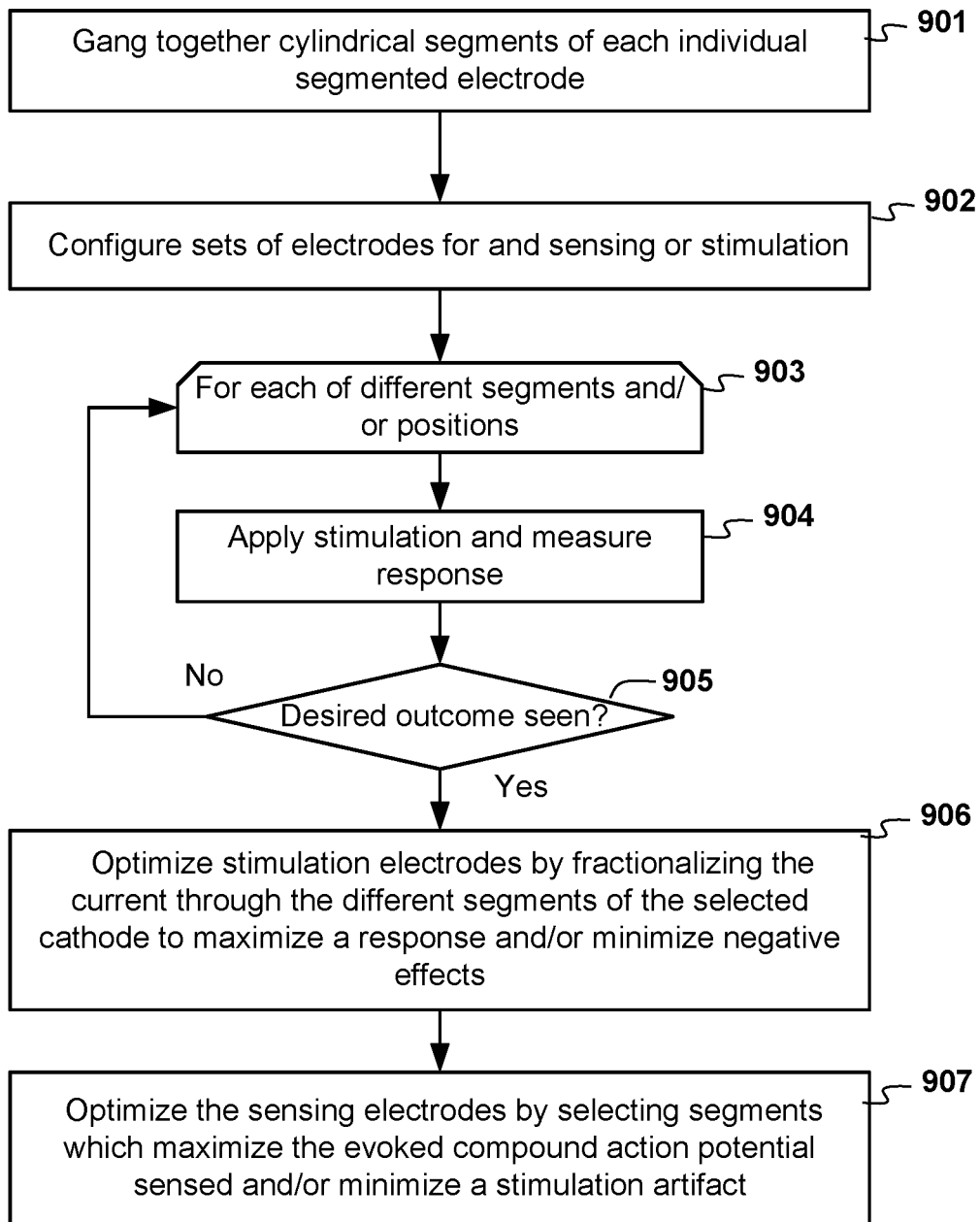
FIG. 9 is a flowchart of a method for configuring an implanted lead with segmented electrodes according to an example embodiment.

In FIG. 9, a flowchart shows a process that facilitates choosing and calibrating electrode segments according to an example embodiment. Generally, the segmented spinal cord stimulation lead is positioned, stimulation and sensing is trialed for a particular set of segmented electrodes, and the sensing/stimulation is optimized by selecting cylindrical segments which maximize particular objectives.

During the method, the lead is positioned to cover the desired anatomy, e.g., targeted region near the spine. The cylindrical segments of each individual segmented electrode are ganged together as indicated in block 901, e.g., via switching circuitry. In block 902, a set of electrodes are configured via a processor for either sensing or stimulation. For example, E7/E6 may be configured as the stimulation cathode/anode, respectively, and E1/E0 may be configured for evoked compound action potential sensing.

Blocks 903-905 represent a sequence to determine an acceptable placement of the lead. As indicated by loop limit, the lead is repositioned and/or alternative sets of electrodes are selected for various combinations. As indicated by block 904, a test stimulation trial program, such as 50 Hz, 150 µs, 10 mA, balanced biphasic stimulation is delivered to E7/E6. As indicated by decision block 905, this is repeated as needed until a desired outcome is achieved. For example, such an outcome may be 30 µV as measured between N1 and P2 of the triphasic ECAP or paresthesia coverage across the right lateral leg.

The stimulation electrodes are optimized as indicated at block 906. This optimization may involve fractionalizing the current through the different segments of the selected cathode so as to maximize (e.g., the size of the ECAP measured on E1/E0) or minimize negative outcomes (e.g., the amount of current needed from the battery to evoke a particular response, and/or the size of a stimulation artifact) a characteristic. The sensing electrodes are optimized as indicated at block 907 by selecting segments which maximize the evoked compound action potential sensed or minimize a stimulation artifact. The optimized parameter determined in this way may be used (e.g., presented via a user interface in an external programming device) to set operational parameters for the implanted lead.

Figure 10:
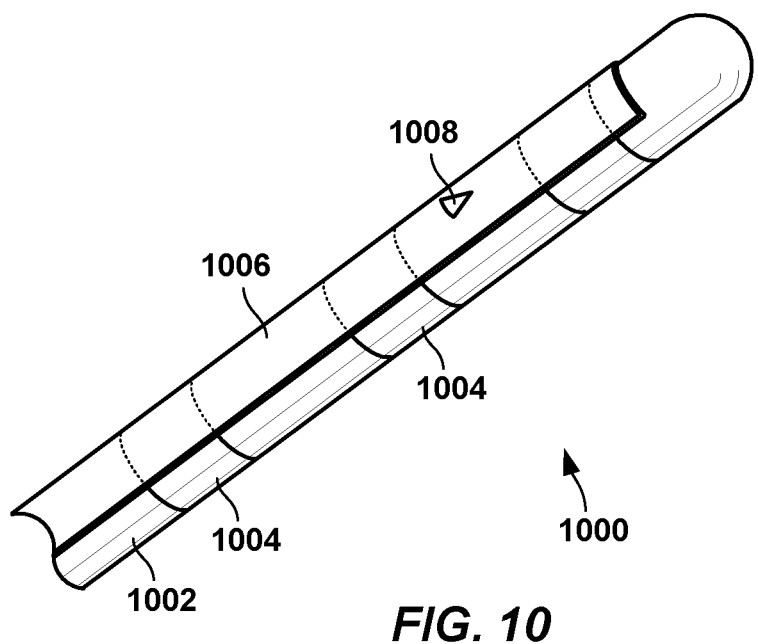
FIG. 10 is an isometric view of a masked lead according to an example embodiment.

In other embodiments, a percutaneous spinal cord stimulation lead may have portions of the cylindrical electrodes masked off to result in segments of the electrodes that are electrically insulated, and/or substituted with cylindrical segments. In FIG. 10, a perspective view shows a masked-type lead 1000 according to an example embodiment.

The lead 1000 includes a lead body 1002, on which are located cylindrical/ring electrodes 1004. A partial circumference of the ring electrodes 1004 is covered with an electrical insulator 1006. The exposed portions of the electrodes 1004 not covered by the insulator 1006 can sense and/or emit normally, while sensing/emission at the covered regions is inhibited. This lead may 1000 also include a radiopaque marker 1008 so as to provide the lead implanter a means to determine alignment.

Some or all of the electrodes 1004 may be processed in a different manner. For example, electrodes 1004 intended for stimulation may be masked and electrodes for sensing may be unmasked. In other embodiments, electrodes intended for stimulation may be masked to result in a 180° opening whereas electrodes for sensing may be masked to result in a 90° opening. Note that masked electrodes 1004 may be used on the same lead as segmented electrodes such as are shown in FIG. 5.

Figure 11:
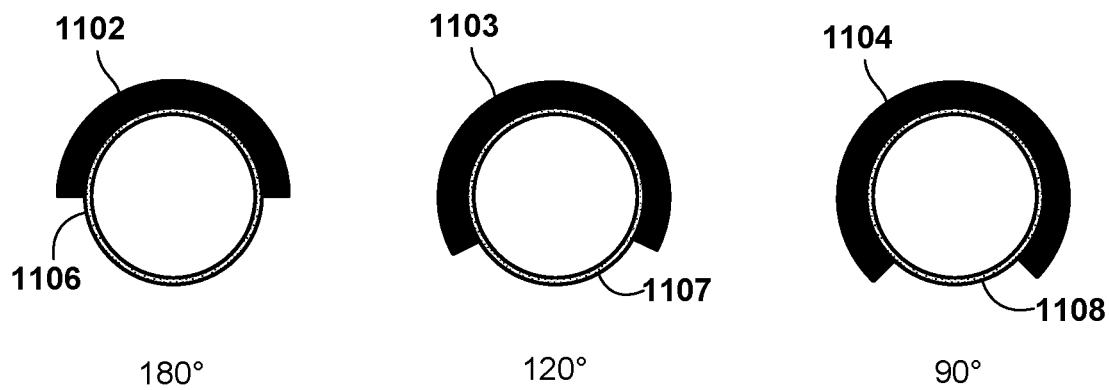
FIG. 11 is a set of cross-sectional views of segmented electrodes according to different example embodiments.

In FIG. 11, cross-sectional views show examples of three different electrodes where portions of each electrode are masked off with an insulator (e.g., polyurethane) to make them electrically insulated. The thick black regions 1102-1104 are the insulation, and the regions 1106-1108 indicate the exposed electrode (e.g., formed of platinum). These examples show three different circumferential angles of the exposed portions 1106-1108, which are 180°, 120°, and 90°, respectively. Any number of different angles may be used, and there may be multiple, discontinuous exposed electrode regions at any given location.

Figure 12:
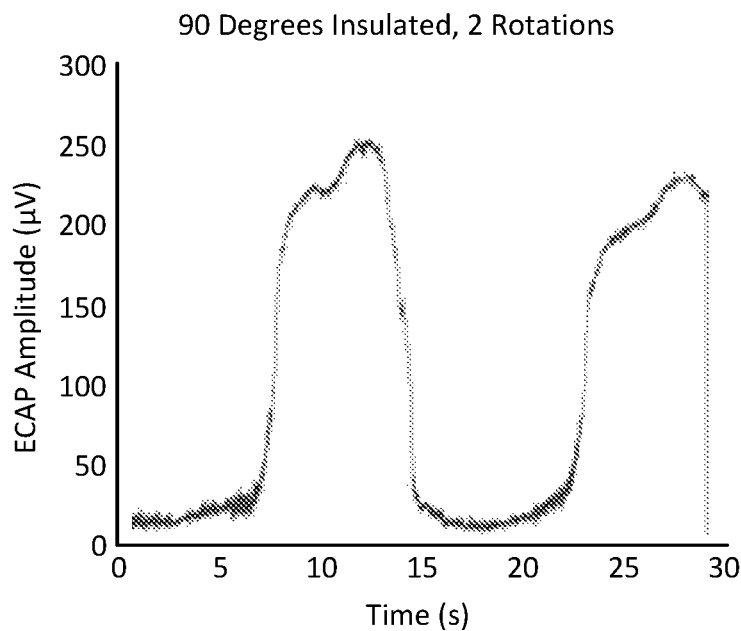
FIGS. 12 and 13 are graphs showing measured results obtained while varying rotation of masked leads according to example embodiments.
Figure 13:
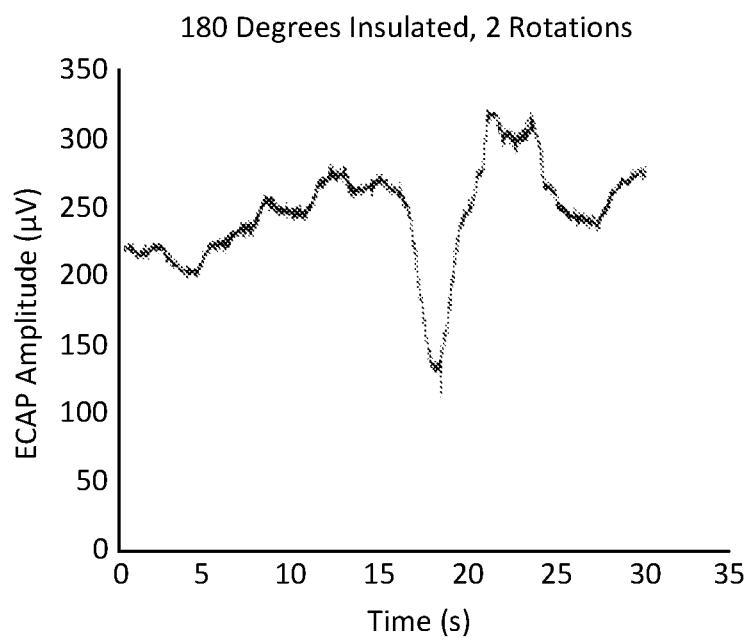

To demonstrate the concept, an eight-electrode compact percutaneous lead was masked with polyurethane to result in either 180° or 90° symmetrical active electrode areas. These leads were placed, one at a time, over the dorsal columns of an ovine spinal cord at T8 via a percutaneous insertion at the thoracolumbar junction. A balanced biphasic stimulation at 50 Hz, 1 mA, 30 µs PW, was delivered on E7(+)/E6(−)/E5 (+) and evoked compound action potentials (ECAPs) were measured on E1(+)/E0(−). An ECAP amplitude was measured for each stimulation pulse. In this case, the ECAP amplitude was the voltage difference between N1 and P2 of the triphasic ECAP. The exteriorized, proximal ends of the leads were then spun through several rotations and ECAP amplitudes were measured concurrently. The results are shown in FIGS. 12 and 13. The leads with a tantalum braid are well-suited for this application because the braid results in a high level of torsional rigidity between the distal and proximal ends of the leads.

Figure 14:
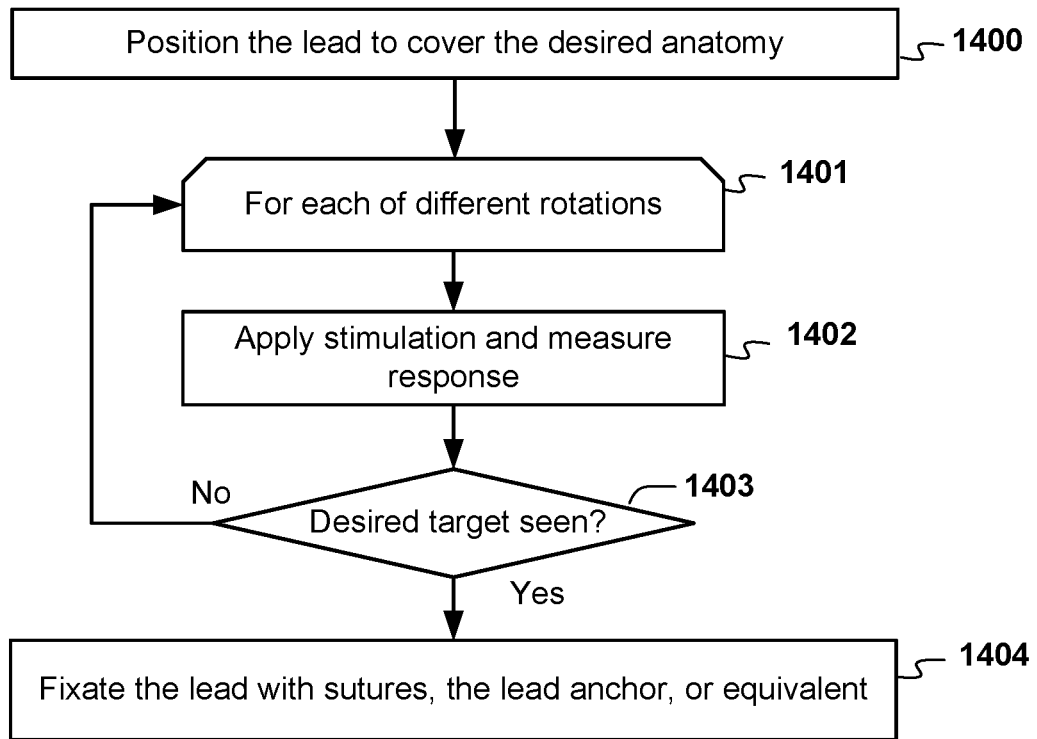
FIG. 14 is a flowchart showing a method for configuring an implanted lead with masked electrodes according to an example embodiment.

In FIG. 14, a flowchart shows a method for placing a masked lead in the recipient according to an example embodiment. Generally, this process may involve a trial and a fixation of the leads. As indicated at block 1400, a lead is positioned to cover the desired anatomy. As indicated by loop limit 1401, the lead body is axially rotated through several "test" orientations while stimulating/recording as indicated at block 1402. This establishes an ECAP maxima/minima.

At block 1403, it is determined via a processor if a desired target is reached. The desired target may be a specific ECAP characteristic, such as particular ECAP amplitude or area under the curve, such as an ECAP of 230 µV with the 90° insulated electrodes. The desired target may also be an offset from a certain point (which may be established in conjunction with the azimuth markers), such as rotation of 180° from the point at which an ECAP of 150 µV is seen with the 180° insulated electrodes. As indicated at block 1404, after the lead has been rotated such that desired target is obtained, the lead may be fixated with sutures, a lead anchor, or equivalent.

Figure 15:
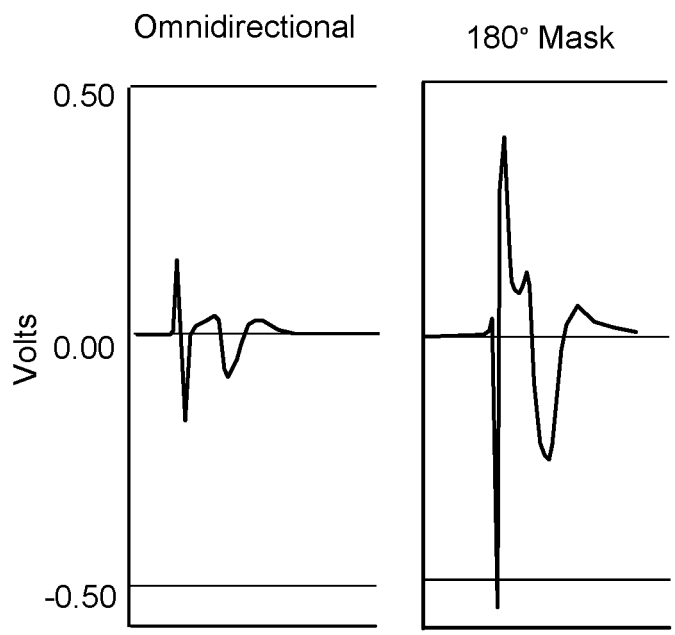
FIG. 15 is a chart comparing output of an omnidirectional lead to that of a masked according to an example embodiment.

Although multiple openings and cylindrical segment sizes are possible, a 180° aperture may provide preferable outcomes between tolerance for rotational misalignment and preferred targeting. In FIG. 15, plots shown the ECAP responses seen for 1 mA, 30 µs, 50 Hz, balanced biphasic stimulation for an omnidirectional (unshielded) and 180° masked lead. Generally, this indicates a much larger neural response for the same current.

A masked electrode as shown in FIGS. 10-11 may be used in some applications described above for segmented electrodes. For example, the configuration for sensing stimulation artifacts shown in FIG. 8 may be accomplished using electrodes that are masked in opposite directions, such that a sensing electrode has an exposed portion facing away from the target tissue and a stimulation electrode has an exposed portion facing the target tissue. In such a configuration, the lead may also have another set of electrodes in proximity to the reverse-facing electrodes, the other set of electrodes facing the target tissue and used to measure ECAP response, for example.

Figure 16:
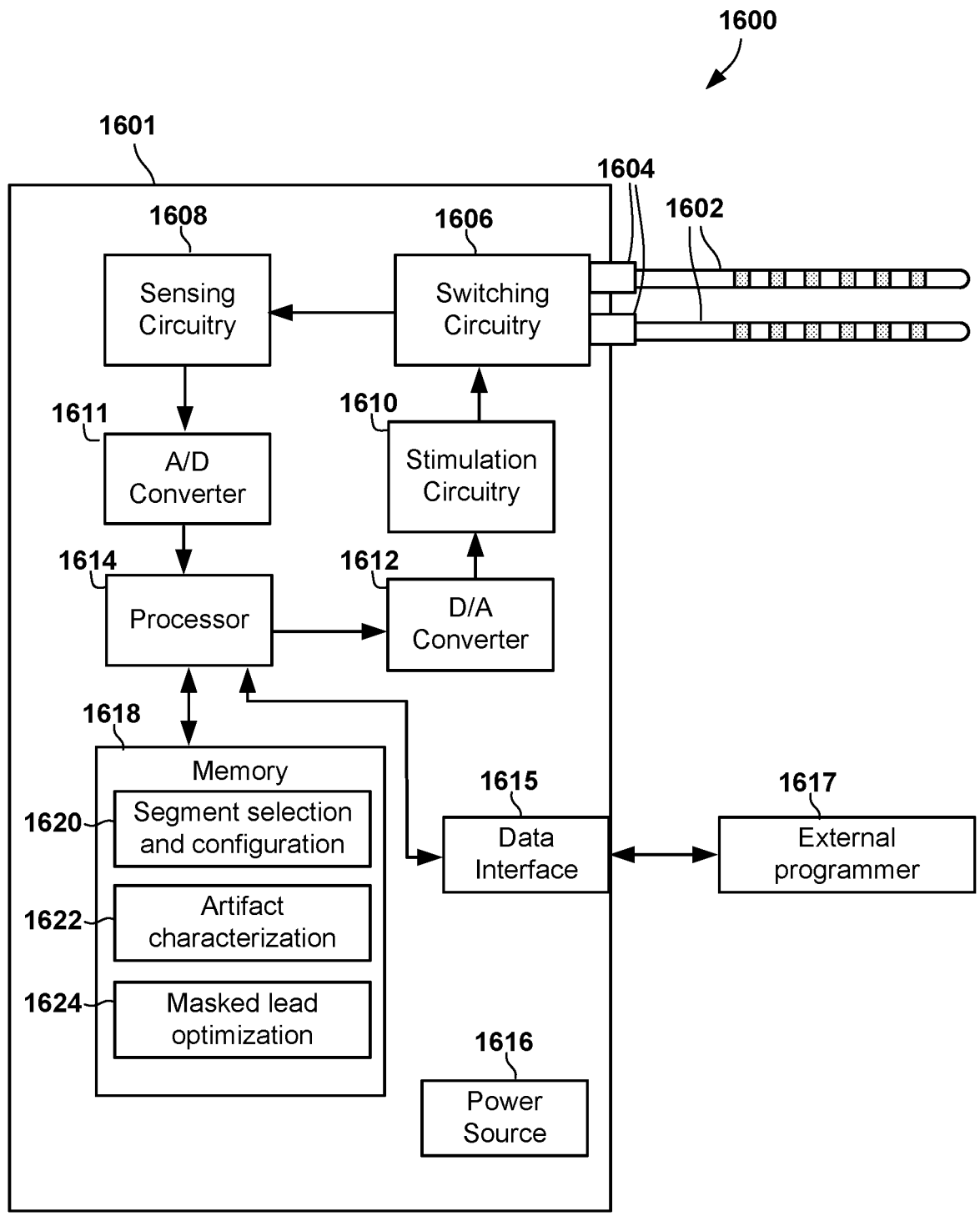
FIG. 16 is a block diagram of an apparatus according to an example embodiment.

In FIG. 16, a block diagram shows an implantable system 1600 according to an example embodiment. The system includes a control unit 1601 which is a self-contained unit that may be implanted within the patient or located externally. One or more leads 1602 are coupled to the control unit 1601 via connectors 1604. The control unit 1601 includes switching circuitry 1606 that selectively couples electrodes (and segments thereof, if so equipped) to individual circuit elements within the control unit 1601. For example, electrodes may be coupled to sensing circuitry 1608 that receives signals generated by electrodes configured as sensing electrodes. Other electrodes (or the same electrodes at different times) may be coupled to stimulation circuitry 1610 that delivers electrical signals (e.g., pulse waveforms) that are delivered to target tissue via the electrodes.

The switching, sensing, and stimulation circuitry 1608, 1610 may include analog processing circuitry such as preamplifiers, amplifiers, filters, etc. As the control unit 1601 may use digital signal processing, the unit 1601 may utilize an analog-to-digital converter 1611 and/or a digital-to-analog converter 1612. These facilitate digital signal processing via one or more processors 1614. The processor may include any combination of central processing units, co-processors, digital signal processors, application specific integrated circuits, etc. The processor 1614 is coupled to memory 1618, which may include any combination of volatile memory (e.g., random access memory) and non-volatile memory (e.g., firmware, flash memory).

The processor 1614 operates in response to instructions stored in the memory 1618. Those instructions may include a segment selection and configuration function 1620 that assists in setup of leads with one or more segmented electrodes, e.g., as shown by way of example in FIG. 9. The instruction may also include a stimulation artifact characterization function 1622 that enables sensors electrodes with exposed or activated surfaces facing away from the target tissue to accurately characterize stimulation artifacts, e.g., as shown in FIG. 8. A masked lead optimization function 1624 may be used to assist in setup of leads with one or more masked electrodes, e.g., as shown by way of example in FIG. 14.

The control unit 1601 may be able to be programmed and/or controlled via an external programmer 1617. The external programmer 1617 links with a data interface 1615 of the device. The data interface 1615 may facilitate communications via any combination of wireless media, wired media, optical media, etc. The external programmer 1617 may send control instructions to the control unit 1610, add software/firmware to the unit 1610, update software/firmware of the unit 1610, and/or download data gathered by the unit 1610. The control unit 1610 may also include a self-contained power source 1616, e.g., battery, capacitors, generator/converter, etc.

This disclosure describes a number of different embodiments, those embodiments including the following:

Embodiment 1 is a system comprising a lead body operable to be implanted proximate a neural pathway of a patient; a sensing electrode configured to sense biopotentials over a first partial circumference of the lead body; a stimulation electrode configured to deliver stimulation energy over a second partial circumference of the lead body; a signal generator electrically coupled to the stimulation electrode; a sensing circuit coupled to the sensing electrode; and a processor coupled to the signal generator and the sensing circuit. The processor is operable to apply a stimulation signal to the stimulation electrode via the signal generator; and via the sensing circuit, sense an evoked response to the stimulation signal that propagates along the neural pathway, wherein the first partial circumference selected to optimize the sensing of the evoked response.

Embodiment 2 includes the system of embodiment 1, wherein the sensing electrode comprises a ring electrode, wherein a first portion of the ring electrode different from the first partial circumference is covered with an electrical insulator that inhibits sensing at the first portion.

Embodiment 3 includes the system of embodiment 1 or 2, wherein the stimulation electrode comprises a ring electrode, wherein a first portion of the ring electrode different from the first partial circumference is covered with an electrical insulator that inhibits electrical field emission at the first portion.

Embodiment 4 includes the system of any of embodiments 1-3, wherein the first and second partial circumferences comprises 270 degrees or less of a circumference of the lead body.

Embodiment 5 includes the system of embodiment 4, wherein the first and second partial circumferences comprise 90 degrees or more of the circumference.

Embodiment 6 includes the system of any of embodiments 1-5, wherein the evoked response comprises an evoked compound action potential (ECAP) response.

Embodiment 7 includes the system of any of embodiments 1-6, wherein the lead body is operable to be implanted in an epidural space of a dorsal column of the patient's spine, and wherein the neural pathway comprises a spinal cord.

Embodiment 8 includes the system of any of embodiments 1-7, wherein the first and second partial circumferences comprise different angles.

Embodiment 9 is a system comprising: a lead body operable to be implanted proximate a neural pathway of a patient; a sensing electrode and a stimulation electrode disposed on the lead body and separated longitudinally along the lead body, both the sensing and stimulation electrodes comprising ring electrodes partially covered with an insulator such the that the ring electrodes sense and emit electrical fields along partial circumferences of the lead body not covered by the insulator; a signal generator electrically coupled to the stimulation electrode; a sensing circuit coupled to the sensing electrode; and a processor coupled to the signal generator and the sensing circuit and operable to: apply a stimulation signal to the stimulation electrode via the signal generator; and via the sensing circuit, sense from the sensing electrode an evoked response to the stimulation signal that propagates along the neural pathway.

Embodiment 10 includes the system of embodiment 9, wherein the partial circumference comprises 270 degrees or less of a circumference of the lead body.

Embodiment 11 includes the system of embodiment 10, wherein the partial circumference comprises 90 degrees or more of the circumference of the lead body.

Embodiment 12 includes the system of any of embodiments 9-11, wherein the evoked response comprises an evoked compound action potential (ECAP) response.

Embodiment 13 includes the system of any of embodiments 9-12, wherein the lead body is operable to be implanted in an epidural space of a dorsal column of a spine of the patient, and wherein the neural pathway comprises a spinal cord.

Embodiment 14 includes the system of any of embodiments 9-13, wherein the processor is further operable to repeatedly perform a test operation over a plurality of rotation angles of the lead body, the test operation comprising for each of the rotation angles: applying a test stimulation signal to the stimulation electrode and sensing from the sensing electrode a test evoked response to the test stimulation signal that propagates along the neural pathway; recording a characteristic of the test evoked response that indicates an effectiveness of at least one of application of the stimulation signal and the sensing of the evoked response at the rotation angle; determining from the characteristics recorded during the test operations, a selected rotation angle of the lead body that results in effective performance of the lead body; and affixing the lead body in the epidural space oriented in the selected rotation.

Embodiment 14A includes the system of any of embodiments 9-14, wherein the lead body comprises a tantalum braid.

Embodiment 15 is a method comprising: repeatedly performing a test operation over a plurality of rotation angles of the lead, the test operation comprising for each of the rotation angles: applying a stimulation signal to the stimulation electrode and sensing from the sensing electrode an evoked response to the stimulation signal that propagates along the neural pathway; recording a characteristic of the evoked response that indicates an effectiveness of at least one of application of the stimulation signal and the sensing of the evoked response at the rotation angle; determining from the characteristics recorded during the test operations, a selected rotation angle of the lead that results in effective performance of the lead; and affixing the lead in the epidural space oriented in the selected rotation.

Embodiment 16 includes the method of embodiment 15, wherein the sensing and stimulation electrodes comprise ring electrodes partially covered with an insulator such that the ring electrodes emit and sense electrical fields along the partial circumferences of the lead.

Embodiment 17 includes the method of embodiment 15 or 16, wherein the evoked response comprises an evoked compound action potential (ECAP) response.

Embodiment 18 includes the method of any of embodiments 15-17, wherein the lead is implanted in an epidural space of a dorsal column of the patient's spine.

Embodiment 19 includes the method of embodiment 18, wherein the neural pathway comprises a spinal cord.

Embodiment 20 includes the method of any of embodiments 15-19, wherein the partial circumferences comprises 270 degrees or less of a circumference of the lead.

Embodiment 21 is an apparatus comprising: circuitry operable to be coupled to a lead implanted proximate a neural pathway of a patient, a sensing electrode and a stimulation electrode being disposed on the lead and separated longitudinally along the lead, both the sensing and stimulation electrodes comprising ring electrodes partially covered with an insulator such the that the ring electrodes sense and emit electrical fields along partial circumferences of the lead not covered by the insulator; and a processor coupled to the circuitry and operable to: apply a stimulation signal to the stimulation electrode via the signal generator; and via the sensing circuit, sense from the sensing electrode an evoked response to the stimulation signal that propagates along the neural pathway.

Embodiment 22 includes the apparatus of embodiment 21, wherein the partial circumferences comprises 270 degrees or less of a circumference of the lead body.

Embodiment 23 includes the apparatus of embodiment 22, wherein the partial circumferences comprises 90 degrees or more of the circumference of the lead body.

Embodiment 24 includes the apparatus of any of embodiments 21-23, wherein the evoked response comprises an evoked compound action potential (ECAP) response.

Embodiment 25 includes the apparatus of any of embodiments 21-24, wherein the lead is operable to be implanted in an epidural space of a dorsal column of a spine of the patient, and wherein the neural pathway comprises a spinal cord.

Embodiment 26 includes the apparatus of any of embodiments 21-25, wherein the partial circumference of the stimulation electrode comprises a different angle than the partial circumference of the sensing electrode.

Embodiment 27 includes the apparatus of any of embodiments 21-26, wherein the lead body comprises a tantalum braid.

The various embodiments described above may be implemented using circuitry, firmware, and/or software modules that interact to provide particular results. One of skill in the arts can readily implement such described functionality, either at a modular level or as a whole, using knowledge generally known in the art. For example, the flowcharts and control diagrams illustrated herein may be used to create computer-readable instructions/code for execution by a processor. Such instructions may be stored on a non-transitory computer-readable medium and transferred to the processor for execution as is known in the art. The structures and procedures shown above are only a representative example of embodiments that can be used to provide the functions described hereinabove.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

The foregoing description of the example embodiments has been presented for the purposes of illustration and description. It is not intended to be exhaustive or to limit the embodiments to the precise form disclosed. Many modifications and variations are possible in light of the above teaching. Any or all features of the disclosed embodiments can be applied individually or in any combination are not meant to be limiting, but purely illustrative.

The invention claimed is:

1. A system comprising:
   a lead body operable to be implanted proximate a neural pathway of a patient;
   a sensing electrode and a stimulation electrode disposed on the lead body and separated longitudinally along the lead body, both the sensing and stimulation electrodes comprising ring electrodes partially covered with an insulator such that the ring electrodes sense and emit electrical fields along partial circumferences of the lead body not covered by the insulator, wherein the partial circumference of the stimulation electrode is a different partial circumference than the partial circumference of the sensing electrode;
   a signal generator electrically coupled to the stimulation electrode;
   a sensing circuit coupled to the sensing electrode; and
   a processor coupled to the signal generator and the sensing circuit and operable to:
     apply a stimulation signal to the stimulation electrode via the signal generator over a plurality of rotation angles of the lead body;
     via the sensing circuit over the plurality of rotation angles, sense from the sensing electrode an evoked response to the stimulation signal that propagates along the neural pathway; and
     select one of the rotation angles based on the evoked response at the selected rotation angle indicating an effectiveness of at least one of application of the stimulation signal and the sensing of the evoked response.

2. The system of claim 1, wherein the partial circumferences comprises 270 degrees or less of a circumference of the lead body.

3. The system of claim 2, wherein the partial circumferences comprises 90 degrees or more of the circumference of the lead body.

4. The system of claim 1, wherein the evoked response comprises an evoked compound action potential (ECAP) response.

5. The system of claim 1, wherein the lead body is operable to be implanted in an epidural space of a dorsal column of a spine of the patient, and wherein the neural pathway comprises a spinal cord.

6. The system of claim 1, wherein the lead body comprises a tantalum braid.

7. The system of claim 1, wherein the partial circumference of the stimulation electrode comprises a stimulation direction and the partial circumference of the sensing electrode comprises a sensing direction, and the stimulation direction and the sensing direction are selectively optimized over a plurality of respective rotation angles for effectiveness of at least one of application of the stimulation signal and the sensing of the evoked response.

8. The system of claim 1, wherein the sensing electrode exhibits at least one of a maximized sensed evoked response and a minimized sensed stimulation artifact at the selected rotation angle.

9. An apparatus comprising:
   circuitry operable to be coupled to a lead implanted proximate a neural pathway of a patient, a sensing electrode and a stimulation electrode being disposed on the lead and separated longitudinally along the lead, both the sensing and stimulation electrodes comprising ring electrodes partially covered with an insulator such that the ring electrodes sense and emit electrical fields along partial circumferences of the lead not covered by the insulator, wherein the partial circumference of the stimulation electrode is a different partial circumference than the partial circumference of the sensing electrode; and
   a processor coupled to the circuitry and operable to:
     apply a stimulation signal to the stimulation electrode via the signal generator over a plurality of rotation angles of the lead body;
     via the sensing circuit over the plurality of rotation angles, sense from the sensing electrode an evoked response to the stimulation signal that propagates along the neural pathway; and
     select one of the rotation angles based on the evoked response at the selected rotation angle indicating an effectiveness of at least one of application of the stimulation signal and the sensing of the evoked response.

10. The apparatus of claim 9, wherein the partial circumferences comprises 270 degrees or less of a circumference of the lead body.

11. The apparatus of claim 10, wherein the partial circumferences comprises 90 degrees or more of the circumference of the lead body.

12. The apparatus of claim 9, wherein the evoked response comprises an evoked compound action potential (ECAP) response.

13. The apparatus of claim 9, wherein the lead body is operable to be implanted in an epidural space of a dorsal column of a spine of the patient, and wherein the neural pathway comprises a spinal cord.

14. The apparatus of claim 9, wherein the lead body comprises a tantalum braid.

15. The apparatus of claim 9, wherein the partial circumference of the stimulation electrode comprises a stimulation direction and the partial circumference of the sensing electrode comprises a sensing direction, and the stimulation direction is different from the sensing direction.

16. The apparatus of claim 9, wherein the sensing electrode exhibits at least one of a maximized sensed evoked response and a minimized sensed stimulation artifact at the selected rotation angle.

17. A method comprising:
repeatedly performing a test operation via a processor over a plurality of rotation angles of a lead coupled to the processor, the lead comprising a sensing electrode and a stimulation electrode disposed on the lead body and separated longitudinally along the lead, both the sensing and stimulation electrodes respectively sensing and emitting electrical fields along partial circumferences of the lead, the test operation comprising performing via the processor for each of the rotation angles:
applying a stimulation signal to the stimulation electrode and sensing from the sensing electrode an evoked response to the stimulation signal that propagates along the neural pathway;
recording a characteristic of the evoked response that indicates an effectiveness of at least one of application of the stimulation signal and the sensing of the evoked response at the rotation angle;
via the processor, determining from the characteristics recorded during the test operations, a selected rotation angle of the lead that results in effective performance of the lead, the selected rotation angle facilitating orientation of the lead affixed in the epidural space.

18. The method of claim 17, wherein the sensing and stimulation electrodes comprise ring electrodes partially covered with an insulator such that the ring electrodes emit and sense electrical fields along the partial circumferences of the lead.

19. The method of claim 17, wherein the evoked response comprises an evoked compound action potential (ECAP) response.

20. The method of claim 17, wherein the lead is implanted in an epidural space of a dorsal column of the patient's spine.

21. The method of claim 20, wherein the neural pathway comprises a spinal cord.

22. The method of claim 17, wherein the partial circumferences comprises 270 degrees or less of a circumference of the lead.

* * * * *